US006417006B1

(12) United States Patent
Sundrehagen

(10) Patent No.: US 6,417,006 B1
(45) Date of Patent: Jul. 9, 2002

(54) ASSAY METHOD FOR CARDIOVASCULAR DISEASE

(75) Inventor: Erling Sundrehagen, Oslo (NO)

(73) Assignee: Axis Shield ASA (NO)

( * ) Notice: Subject to any disclaimer, the term of this patent is extended or adjusted under 35 U.S.C. 154(b) by 0 days.

(21) Appl. No.: 09/708,851

(22) Filed: Oct. 5, 2000

Related U.S. Application Data

(63) Continuation of application No. PCT/GB99/02752, filed on Aug. 19, 1999.

(30) Foreign Application Priority Data

Aug. 20, 1998 (GB) ............................................. 9818237
Jan. 25, 1999 (GB) ............................................. 9901583

(51) Int. Cl.⁷ ............................................. G01N 33/20
(52) U.S. Cl. ............................. 436/84; 436/93; 436/96; 422/61
(58) Field of Search ............................. 436/63, 84, 91, 436/92, 93, 96, 505, 811; 422/61

(56) References Cited

U.S. PATENT DOCUMENTS 4,273,757 A * 6/1981 Selhub et al. ............... 436/505
4,680,273 A    7/1987 Herbert
6,066,467 A * 5/2000 Xu et al. ....................... 435/23

FOREIGN PATENT DOCUMENTS

WO    WO 95/15750 A1    6/1995

OTHER PUBLICATIONS

Abstract AN 1997:307508 Biosis—Flynn et al. *Journal of the American College of Nutrition,* vol. 16, No. 3, pp. 258–267, 1997.*
Flynn et al., "Atherogenesis and the Homocysteine–Folate–Cobalarrin Triad: Do We Need Standardized Analysis?", Journal of the American College of Nutrition, vol. 16, No. 3, 258–267 (1997).
van Kapel, J. et al.; "Application of heparin–conjugated Sepharose for the measurement of cobalamin–saturated and unsaturated taranscobalamin II", Clinica Chimica Acto, 172 (1988) 297–310, Elsevier.

* cited by examiner

*Primary Examiner*—Maureen M. Wallenhorst
(74) *Attorney, Agent, or Firm*—Karen Lee Orzechowski; Liniak, Berenato, Longacre & White, LLC

(57) ABSTRACT

An assay method for detecting potential cardiovascular disease (CVD) in a vascularized subject by assessing the concentration of holo-transcobalamin II (holo-TCII) in a sample from the subject where abnormally low levels of holo-TCII are indicative of CVD or susceptibility to CVD.

14 Claims, No Drawings

ASSAY METHOD FOR CARDIOVASCULAR DISEASE

This application is a continuation of International Application No. PCT/GB99/02752, filed Aug. 19, 1999 (status—pending).

BACKGROUND OF THE INVENTION

The present invention relates to an assay method for detecting potential cardiovascular disease (CVD) in a vascularized subject, e.g. a human or non-human animal, especially a mammal, and in particular to an assay method which may be used to detect potential cardiovascular disease before the onset of CVD symptoms noticeable by the subject.

Cardiovascular disease is a major source of ill health among the human, population yet early or preemptive treatment, e.g. with change of diet, reduction or cessation of smoking, increase in regular exercise, prescription of lipid lowering drugs, etc., has a high success rate.

There is accordingly a need for methods which can be used to detect CVD or the potential for or propensity to CVD before the disease has progressed beyond the stage where treatment is routinely successful or may be used to prevent further progression of the disease, and in particular to detect CVD at the early stages when the symptoms are, not apparent to the patient or his physician.

Such methods may be used to screen the general population, or at-risk groups within the population, e.g. males over 40, workers in high stress jobs, patients with unhealthy diets, smokers, etc. where potential CVD or propensity to CVD is diagnosed, preemptive treatment may be given and/or the patient may be encouraged to make adjustments to lifestyle and habits. Likewise, where CVD, potential CVD or propensity to CVD is detected, the patient may be submitted to further testing, e.g. using more expensive or time consuming techniques, such as ECG, with and. without physical activity, radioisotope imaging of myocardial perfusion, X-ray (e.g. CT) myocardial angiography, MR myocardial angiography or perfusion imaging, etc. to confirm the presence and status of CVD. By the use of such assay methods as a "coarse filter" screening technique, unnecessary use of such expensive and time-consuming tests may be avoided while still increasing the. likelihood of as-yet undiscovered CVD being found and treated before health damage becomes irreversible.

SUMMARY OF THE INVENTION

The present invention is based on the realization that the protein complex holo-transcobalamin II, (holo TCII) a complex of the carrier protein transcobalamin II (TCII) and Vitamin $B_{12}$ (cobalamin) is at efficient marker for cardiovascular disease, and in particular that abnormal low holo-TCII levels in body fluids such as blood is indicative of CVD or susceptibility to CVD.

For the avoidance of doubt, the term "cobalamin" is used herein synonymously with "vitamin $B_{12}$" and includes all forms of vitamin $B_{12}$ (e.g. cyanocobalamin; 5-6-dimethylbenzimidazolyl cyanocobamide; methylcobalamine; 5'-deoxyadenoaylcobalamin) as may occur and be metabolically active (when appropriately presented) in the body.

DETAILED DESCRIPTION OF THE INVENTION

Vitamin $B_{12}$ (cobalamin) is a water soluble vitamin which forms part of the vitamin B complex found in foods. The core molecule consists of a corrin ring of four pyrole units which surround the essential cobalt atom. Cobalamin is the only vitamin which cannot be synthesised by animals or plants and must be absorbed from food in the gut. It can however be stored in the liver. It is synthesised by micro-organisms, in particular by anaerobic bacteria and yeasts.

Cobalamin functions in vivo as a co-enzyme and cobalamin enzymes catalyse three types of reaction: (i) intramolecular rearrangements; (ii) methylations; and (iii) reduction of ribonucleotides to deoxyribonucleotides in some micro-organisms. In mammals, only two enzymic reactions, namely (i) and (ii) above, are known to require cobalamin as a co-enzyme.

In the process of digestion, a salivary protein called haptocorrin (which is also referred to in the art as R-binder or transcobalamins I and III collectively) binds cobalamin in the upper gastrointestinal tract forming a complex which passes through the stomach. Pancreatic enzymes digest the cobalamin-haptocorrin complex in the ileum, liberating cobalamin which is then bound to a protein called intrinsic factor, which is secreted by the gastric mucosa, to form a further complex. The cobalamin-intrinsic factor complex binds to a specific receptor in the lining of the terminal ileum, whereupon it is dissociated by a releasing factor and the cobalamin is transported actively across the membrane of the ileum into the blood stream.

Cobalamin does not circulate in the body in a free form in any appreciable amount. Probably 99% or so of cobalamin is bound by one of the transcobalamin proteins (TC I, II and III) or albumin.

The protein believed to be solely responsible for transporting cobalamin to target tissues is transcobalamin II (TCII), a critical trace protein without which cobalamin cannot cross cell membranes. Despite this important metabolic function, only about 6–25% of cobalamin in the serum is bound to TCII—most is carried by haptocorrin. TCII comprises a single chain polypeptide of about 40 kDa found primarily in serum, seminal fluid and cerebro-spinal fluid. Cobalamin bound TCII (i.e. holo-TCII) attaches to specific receptors on cell membranes and, once bound, the holo-TCII is taken into cells by pinocytosis. The holo-TCII constitutes the metabolically active pool of cobalamin, since none of the other cobalamin binding proteins, including transcobalamins I and III, are able to facilitate entry of the vitamin into cells.

TCII is synthesised by the liver, vascular endothelium, enterocytes, macrophages and fibroblasts and circulates predominantly as apo-TCII, i.e. lacking bound cobalamin. It has a short half life of approximately 90 minutes.

Less than about a quarter of the total plasma cobalamin is associated with TCII. The rest is bound to the other transcobalamins or albumin as mentioned above. The function or role of the non-TCII transcobalamins is unclear, but since they bind both cobalamin and cobalamin-like substances, they may play a role in ensuring that potentially harmful analogues of cobalamin cannot compete with cobalamin by virtue of them being unable to enter cells if bound to TC I or III. They may play a role in removing cobalamin analogues from the circulation or may serve as a store of cobalamins. Alternatively, they may ensure that free cobalamin and analogues thereof are not available for utilisation by micro-organisms.

Thus viewed from one aspect the invention provides an assay method for the detection of cardiovascular disease (CVD), potential cardiovascular disease, or propensity to cardiovascular disease in a human or non-human animal subject, said method comprising assessing the concentration of holo-transcobolamin II (holo TCII) in a cobalamin containing sample from said subject, e.g. a sample of blood, plasma, serum, seminal fluid, amniotic fluid or cerebrospinal fluid, preferably a sample of blood, plasma or serum, in particular a sample of serum.

By assessing it is meant that a quantitative or semi-quantitative value for the concentration of holo-TCII is determined. This may be a value for the concentration of the sample as tested, e.g. after treatment to remove cells or other sample components not being assayed for, or to concentrate or dilute the sample or to transfer the holo-TCII to a separate medium, e.g. a solid substrate.

Alternatively, the assessment may simply be qualitative, ie. to indicate whether the holo-TCII concentration is above or below one or more pre-selected threshold values, e.g. values indicative of absence of CVD detectable by the assay, presence of CVD (or potential CVD or propensity to CVD) as detectable by the assay, or uncertainty as to presence or absence of CVD, etc. The precise values for such threshold values or other reference values for holo-TCII concentration may depend on the nature of the sample, the age, weight, sex and species of the subject and may be determined in a routine manner by testing equivalent subjects without CVD or with CVD at various stages of development.

A value indicative of holo-TCII concentration determined (or "assessed") in accordance with the method of the invention may be an absolute concentration of holo-TCII or may alternatively be an index, ratio, percentage or similar indication of the concentration of holo-TCII and that of some other analyte, e.g. another transcobolamin or homocysteine. A preferred ratio is that between the concentration of holo-TCII and the total cobolamin concentration. Total cobolamin assays are known from the literature as are assays for other analytes such as homocysteine which was mentioned above.

The body sample used in the assay method of the invention may be any cobalamin containing sample, e.g. a body fluid or tissue sample, or a suspension etc. Generally the sample will not be urine or a sample taken from the gastrointestinal tract. Preferably, the sample will be a body fluid for example, seminal fluid, cerebro-spinal fluid or amniotic fluid, or more particularly blood or a blood derived sample. When this is the case, the sample used for analysis will preferably be cell-free and hence either serum or plasma may be used. The sample may be treated prior to being used in the assay method of the invention, for example it may be diluted by adding a buffer or other aqueous medium.

While assays for holo-TCII are known and may be used in the method of the invention, there has not previously been any suggestion that holo-TCII is a marker for CVD or propensity to CVD.

Examples of holo-TCII assays are described or referenced for example in: Herzlich et al., Lab. Invest. 58: 332–337 (1988); Markle, Critical Reviews in Clinical Laboratory Sciences 33: 247–356 (1996); Herbert, Am. J. Clin. Nutrition 59 (5 Suppl.): 1213S-1222S (1994); Das et al., J. Nutr. Biochem. 2: 455–464 (1991); van Kapel et al., Clin. Chim. Acta 172: 297–310 (1988); Lindemans et al., Clin. Chim. Acta 132: 53–61 (1983); Nexø et al., Scand. J. Lab. Invest 37: 723–728 (1997); Morelli et al., J. Lab. Clin. Med. 89: 645–652 (1977); Carmel, Am. J. Clin. Pathol. 62: 367–372 (1974); Wickramasinghe et al., J. Clin. Pathol. 46: 537–539 (1993); Vu et al., Am. J. Hematol. 42: 202–211 (1993); Benhayoun et al., Acta Haematol. 89: 195–199 (1993); Rothenberg et al., Methods in Enzymology 281: 261–268 (1997); and in Frater-Schrader et al., pages 877–880 in "Vitamin $B_{12}$", Zagalak et al (Ed), W. De Gruyter, Berlin, 1979.

Thus for example van Kapel et al. (supra) disclose a method for specifically separating TCII from other transcobalamins using heparin sepharose, thus facilitating the quantitation of holo-TCII by radioisotope dilution assay and the concentration of non-cobalamin carrying TCII by measuring the unsaturated cobalamin binding capacity of the bound TCII with radioactive cobalamin. Similar methods using microfine silica such as QUSO™ have been used to bind TCII and allow its purification (in either apo or holo form) from TC I and III (see Das et al. (supra)). It is thought however that heparin sepharose is a more specific binder of TCII and some researchers have reported that TC I and III bind to silica in appreciable amounts (see Benhayoun et al. Acta Haematol. 89:195–199 (1993)). Toft et al. Scand. J. Clin. Lab. Invest. 54:62 (1994)) have recently proposed a method whereby transcobalamin II is adsorbed to cellulose and the cobalamin associated with the bound TCII may be quantified by standard methods.

An immunoassay for holo-TCII in which sepharose anti-TCII is used as described in Lindemans (supra) which uses a technique described by Lindemans et al. in Clin. Chim. Acta 95: 29–33 (1979).

The method currently used in clinical practice for determining holo-TCII involves adsorbing TCII to silica and then assaying the bound fraction for cobalamin content using either an immunoassay (as described for example by Kuemmerle et al. Clin. Chem. 38/10: 2073–2077 (1992) or a microbiological assay, the latter apparently producing the best results. This method is accurate and reliable.

In general, besides the sample under evaluation, calibration samples with known holo-TCII content will also be assessed in the performance of the assay method. Such determinations can be used to plot a calibration curve from which the holo-TCII content of the sample under investigation may be determined. The nature of the calibration samples and selection of conversion or adjustment factors used in the determination of the holo-TCII may vary depending, for example, on the manner in which holo-TCII is detected in the assay technique actually used and on other aspects of the method which affect the assay result, for example, buffer composition, assay conditions etc. Typically, calibration samples having holo-TCII contents of 0 to 300 pmol/L will be used. The reference range within which the value for holo-TCII will generally be found is 0 to 160 pmol/L. A holo-TCII concentration in serum below 35 pmol/L will generally be strongly indicative of deficiency.

A set of cobalamin standards, preferably with an extended concentration range of 80 to 800 pmol/L or broader, e.g. 0 to 1500 pmol/L, may be used to determine the total cobalamin content of the sample, and not just the holo-TCII content, if such a measurement is required.

Besides obtaining a determination of holo-TCII content for the sample under investigation, it may frequently be desirable to determine the total cobalamin content in the sample and/or the apo-TCII content in the sample. Many of the publications referred to above describe how this may be done.

In general, serum total cobolamin content for humans will be in the range 200–600 pmol/L and holo, TCII content will normally represent some 6 to 20% of this, ie. 30–160 pmol/L. A threshold value below which the assay may be held to be predictive of CVD or CVD propensity may generally be about 35 pmol/L, more preferably about 30 pmol/L especially about 20 pmol/L.

However, the threshold values are better calculated from holo-TCII determinations using the same assay technique for the same body sample type from a range of patients of similar type (age, sex, weight, species, etc.) from healthy through early stage CVD to serious CVD. Even more preferably, the threshold values will be values determined for the same patient at an earlier, healthy stage.

Viewed from a further aspect, the present invention provides an assay kit for use in the method of the invention, said kit comprising reagents and instructions for the performance of the assay method and for the interpretation of the results and, optionally, holo-TCII containing reference samples, and optionally, a detector.

The instructions in the kit may for example be in the form of a label, a manual or an instruction leaflet; however they may instead take the form of a computer program or a data carrier, e.g. a computer disc.

The detector, where present, will generally be one capable of detecting a reporter species, e.g. a spectrometer, a nuclear radiation detector, a scattered light detector, etc.

The reagents will be reagents suitable for holo-TCII determination, e.g. reagents as specifie d in t he literature cited herein which relates to holo-TCII determination.

The invention will now be described in the following non-limiting example:

EXAMPLE 1

Clinical Study on Holo-TCII and Cardiovascular Disorders

Holo-TC II and homocysteine levels were m easured in serum samples taken from (i) 25 healthy volunteers, (ii) 90 PTCA (Percutaneous Transluminal Coronary Angioplasty) patients prior to procedure, and (iii) 80 myocardial infarct patients six days after infarct and for 37 of the se also six weeks after infarct.

Holo-TC II was measured using the non-specific method of adsorption of TC II on silica (Toft et al. (1994) Scand. J. Clin. Lab. Invest. 54: 62–63) and homocysteine by the IMx method developed by Axis (Shipchandler & Moore (1995) Clin. Chem. 41: 991–994).

35 pM was defined as the cut-off for holo-TC II; values below 35 pM being considered as deficient. For homocysteine 14.6 pM was defined as the cut-off; values below 14.6 pM were considered to be within the normal range.

As an estimate of risk, odds ratios were calculated as follows: cases with "out or norm al" values/total cases of the disorder divided with the same ratio for the control group.

A value greater than one (1) indicates that a risk may exist.

| | | Holo-TC II | | Homocysteine | |
|---|---|---|---|---|---|
| Group | Total | Cases | Odds Ratio | Cases | Odds Ratio |
| Control | 25 | 1 | — | 1 | — |
| PTCA | 90 | 5 | 1.4 | 19 | 5.3 |
| MI, day 6 | 80 | 2 | 0.6 | 30 | 9.4 |
| MI, week 6 | 37 | 4 | 2.7 | 15 | 10 |

The odds ratio for homocysteine are in accordance with numerous other studies showing that homocysteine values higher than about 15 $\mu$M are associated with a greater risk for cardiovascular disease.

The odds ratio for holo-TC II indicate that such a risk, albeit lower pertain also to holo-TC II. The values are probably underestimated because of the non-specific method used, adsorption of TC to silica. The oods ratio smaller than unity observed for MI at day 6 is most likely due to TC II being an acute phase protein and thus may be expected to increase in concentration after trauma such as a myocardial infarct. The increased concentration of TC II will cause a temporary redistribution of cobalamin from haptocorrin to TC II, masking any underlying chronic decrease in holo-TC II.

What is claimed is:

1. An assay method for the detection of cardiovascular disease (CVD), potential cardiovascular disease (potential CVD), or propensity to cardiovascular disease (propensity for CVD) in a human or non-human animal subject, said method comprising assessing the concentration of holo-transcobalamin II (holo-TCII) in a cobalamin containing body sample from said subject and comparing the assessed concentration with a holo-TCII threshold value below which the assay is held to be predictive of CVD, potential CVD or propensity to CVD.

2. A method as claimed in claim 1 wherein said cobalamin containing body sample is a blood sample.

3. A method as claimed in claim 2 wherein said cobalamin containing body sample is a serum sample.

4. A method as claimed in claim 1 wherein said cobalamin containing body sale is a serum sample.

5. A method as claimed in claim 1 wherein said cobalamin containing body simple is treated prior to use in the assay method to separate the holo-TCII.

6. A method as claimed in claim 1 wherein a value of 35 pmol/l holo-TCII or below is predictive of CVD, potential CVD or CVD propensity.

7. A method as claimed in claim 6 wherein a value of 20 pmol/l holo-TCII or below is predictive of CVD, potential CVD or CVD propensity.

8. A method as claimed in claim 1 wherein the holo-TCII threshold value for predicting CVD, potential CVD or CVD propensity is calculated using the same assay method for the same cobalamin containing body sample type from a range of subjects of similar type.

9. A method as claimed in claim 1 wherein a total cobalamin content and/or apo TCII content in the sample are also measured.

10. An assay kit for use in a method according to claim 1, said kit comprising reagents and instructions for the performance of the assay method and for the interpretation of the results.

11. An assay kit as claimed in claim 10 additionally comprising holo-TCII containing reference samples.

12. An assay kit as claimed in claim 10 additionally comprising a detector.

13. A method as claimed in claim 1 wherein the assessed concentration and the holo-TCII threshold value are compared by a method selected from quantitative comparison, semi-quantitative comparison, and qualitative comparison.

14. An assay method for the detection of cardiovascular disease (CVD), potential cardiovascular disease (potential CVD), or propensity to cardiovascular disease (propensity for CVD) in a human or non-human animal subject, said method comprising measuring a value indicative of holo-TCII concentration in a sample taken from said subject and comparing said value with a threshold value below which the assay is held to be predictive of CVD, potential CVD, or propensity for CVD wherein the value indicative of holo-TCII concentration measured is a ratio between holo-TCII concentration and a total cobalamin concentration in said sample.

* * * * *

UNITED STATES PATENT AND TRADEMARK OFFICE
CERTIFICATE OF CORRECTION

PATENT NO. : 6,417,006 B1
DATED : July 9, 2002
INVENTOR(S) : Erling Sundrehagen

It is certified that error appears in the above-identified patent and that said Letters Patent is hereby corrected as shown below:

<u>Column 6,</u>
Line 25, "sale" should read -- sample --.
Line 27, "simple" should read -- sample --.

Signed and Sealed this

Nineteenth Day of August, 2003

JAMES E. ROGAN
*Director of the United States Patent and Trademark Office*